| United States Patent [19] | [11] | 4,408,080 |
|---|---|---|
| Isogai et al. | [45] | Oct. 4, 1983 |

[54] PROCESS FOR PRODUCING ACETALDEHYDE

[75] Inventors: Nobuo Isogai; Motoyuki Hosokawa; Takashi Okawa; Natsuko Wakui; Toshiyasu Watanabe, all of Niigata, Japan

[73] Assignee: Mitsubishi Gas Chemical Company, Inc., Tokyo, Japan

[21] Appl. No.: 274,360

[22] Filed: Jun. 16, 1981

[30] Foreign Application Priority Data

Jun. 18, 1980 [JP] Japan .................................. 55-82299

[51] Int. Cl.$^3$ ........................ C07C 47/06; C07C 45/49
[52] U.S. Cl. .................................... 568/484; 568/485; 568/487
[58] Field of Search .................... 568/484, 485, 487

[56] References Cited

U.S. PATENT DOCUMENTS

| 4,151,208 | 4/1979 | Pretzer et al. | 568/487 |
|---|---|---|---|
| 4,190,729 | 2/1980 | Forster | 568/487 |
| 4,225,517 | 9/1980 | Gane | 568/487 |
| 4,239,704 | 12/1980 | Pretzer et al. | 568/487 |
| 4,252,741 | 2/1981 | Porcelli et al. | 568/484 |
| 4,262,154 | 4/1981 | Gane et al. | 568/487 |
| 4,293,718 | 10/1981 | Gauthier-Lafaye et al. | 568/487 |
| 4,302,611 | 11/1981 | Porcelli | 568/484 |
| 4,306,091 | 12/1981 | Gauthier-Lafaye et al. | 568/489 |

FOREIGN PATENT DOCUMENTS

| 41-15692 | 5/1966 | Japan | 568/484 |
|---|---|---|---|
| 48-4003 | 5/1973 | Japan | 568/484 |

*Primary Examiner*—Werren B. Lone
*Attorney, Agent, or Firm*—Wenderoth, Lind & Ponack

[57] ABSTRACT

In a process for producing acetaldehyde which comprises reacting a mixture of methanol and methyl acetate with carbon monoxide and hydrogen in the presence of a cobalt-iodine catalyst, the improvement wherein methyl acetate is used in an amount of 0.4 to 9 parts by weight per part by weight of methanol, cobalt and iodine are used in an amount of 2 to 100 milligram-atoms and 8 to 200 milligram-atoms, respectively, per mole of the entire methyl groups in the methanol and methyl acetate, 1 to 4 iodine atoms being present per cobalt atom, and the reaction is carried out at a temperature lower than 160° C. and a pressure of not more than 300 kg/cm$^2$.

5 Claims, No Drawings

PROCESS FOR PRODUCING ACETALDEHYDE

This invention relates to a process for producing acetaldehyde by reacting a mixture of methanol and methyl acetate with carbon monoxide and hydrogen.

A method is known to produce acetaldehyde by reacting a mixture of methyl acetate and methanol with carbon monoxide and hydrogen (Japanese Patent Publication No. 15692/1966). This method comprises reacting a gaseous mixture of methanol, carbon monoxide and hydrogen in the presence of a cobalt catalyst promoted by a halogen or a halogen compound at a temperature of 160° to 230° C. and a pressure of 200 to 1,000 kg/cm$^2$ to form acetaldehyde or ethanol, characterized in that methyl acetate is added to the starting methanol. In the above method, the proportion of methyl acetate added to the starting methanol is up to 50% by weight, and the proportion of the catalyst is not more than 20 milligram-atoms for the cobalt catalyst and not more than 10 milligram-atoms for the halogen element per mole of methanol. This serves to inhibit formation of methyl acetate from methanol and to increase formation of ethanol and acetaldehyde components (acetaldehyde and dimethoxyethane).

It is difficult, however, to selectively produce acetaldehyde under the conditions disclosed in the prior art. Ethanol, acetic acid, ethyl acetate, etc. are formed as by-products. Formation of by-product methyl acetate can be inhibited to some extent but not completely. Furthermore, high-boiling products inevitably form by the reaction of the resulting acetaldehyde. Consequently, the selectivity for acetaldehyde containing dimethoxyethane is on the order of 60% at the highest.

It is an object of this invention therefore to overcome the difficulties of the prior art, and to provide a process for selectively producing acetaldehyde alone by reacting a mixture of methanol and methyl acetate with carbon monoxide and hydrogen in the presence of a cobalt-iodine catalyst.

The present inventors made extensive investigations in order to achieve the object of the invention, and found that by using a starting mixture consisting of methanol and a suitable amount of methyl acetate and selecting suitable reaction conditions, the methyl groups of the starting mixture can be almost completely converted to acetaldehyde components.

According to this invention, there is provided, in a process for producing acetaldehyde which comprises reacting a mixture of methanol and methyl acetate with carbon monoxide and hydrogen in the presence of cobalt-iodine catalyst, the improvement wherein methyl acetate is used in an amount of 0.4 to 9 parts by weight per part by weight of methanol, cobalt and iodine are used in an amount of 2 to 100 milligram-atoms and 8 to 200 milligram-atoms, respectively, per mole of the entire methyl groups in the methanol and methyl acetate, 1 to 4 iodine atoms being present per cobalt atom, and the reaction is carried out at a temperature lower than 160° C. and a pressure of not more than 300 kg/cm$^2$.

In the mixed starting material used in the process of this invention, the amount of methyl acetate is 0.4 to 9 parts by weight, preferably 0.5 to 4 parts by weight, per part by weight of methanol. If the amount of methyl acetate is smaller than the specified limit, the selectivity for acetaldehyde components is reduced. If, on the other hand, it is larger than the specified limit, the conversion of the methyl groups decreases.

The cobalt catalyst used in the process of this invention may be added in any form. For example, there are widely used metallic cobalt, dicobalt octacarbonyl, cobalt formate, cobalt acetate, cobalt naphthenate, cobalt carbonate, cobalt hydroxide and other various cobalt salts of complexes. Cobalt iodide, however, is preferred. The amount of the cobalt catalyst is 2 to 100 milligram-atoms, preferably 5 to 50 milligram-atoms, per mole of the methyl groups in the mixed starting material.

Examples of iodine sources to be combined with the cobalt catalyst are molecular iodine, sodium iodide, potassium iodide, lithium iodide, calcium iodide, potassium periodate, and various other iodides and iodine-containing compounds. When cobalt iodide is used as the cobalt catalyst, it is not necessary to use such an iodine source.

The amount of iodine added is 8 to 200 milligram-atoms, preferably 10 to 100 milligram-atoms, per mole of the methyl groups of the mixed starting material.

The ratio between cobalt and iodine for conveniently performing the process of this invention is such that 1 to 4 iodine atoms, preferably 1.5 to 2.5 iodine atoms, are present per cobalt atom. If the ratio is lower, the rate of the reaction decreases, and ethanol tends to form as a by-product. At higher ratios, acetic acid tends to occur as a by-product, and production of other high-boiling substances tends to increase. Furthermore, when molecular iodine is used and the atomic ratio of iodine to cobalt is well over 2, the catalyst has an increased corrosive action, and iodine tends to dissipate. For this reason, the atomic ratio of iodine to cobalt is preferably in the vicinity of 2. In order to practice the process of this invention satisfactorily on an industrial scale while inhibiting reactor corrosion and recovering the catalyst, cobalt iodide is simplest in form and most useful.

The reaction conditions described below are suitable for the highly selective production of acetaldehyde components by reacting a mixture of methanol and methyl acetate with carbon monoxide and hydrogen by the process of this invention.

The reaction pressure is from 50 to 300 kg/cm$^2$, preferably 150 to 250 kg/cm$^2$. If it is lower than the specified limit, the reaction does not easily proceed. If it is higher than the specified limit, side-reactions to form ethanol, acetic acid, etc. are accelerated undesirably.

The reaction temperature is from 80° to 160° C., preferably 115° to 155° C. If the temperature is too low, the reaction does not proceed smoothly. If it is higher than the specified limit, formation of by-product ethanol, acetic acid, ethyl acetate, etc. and formation of by-product high-boiling materials increase undesirably.

The gaseous mixture of carbon monoxide and hydrogen used is an ordinary synthesis gas having an H$_2$/CO mole ratio of from ¼ to 4, preferably from ⅔ to 2.

When the process of this invention is carried out under the aforesaid reaction conditions, the selectivity of the methyl groups reacted in the mixture of methanol and methyl acetate for acetaldehyde components is extremely high, and the process is industrially useful.

The process of this invention can be carried out either batchwise or continuously.

EXAMPLES 1 TO 5 AND COMPARATIVE EXAMPLES 1 TO 5

A 100 ml. shaking autoclave made of Hastelloy was charged with a starting mixture of methanol and methylacetate, and a catalyst, and synthesis gas (H$_2$:CO=- about 1) was continuously introduced into the autoclave. The reaction pressure was maintained at 198 kg/cm², and the reaction was carried out at each of the temperatures and for each of the time periods shown in Tables 1 and 2. After the reaction, the autoclave was cooled with ice. The contents were withdrawn, and the intended products were quantitatively determined by gas chromatography.

The results are shown in Tables 1 and 2.

The conversion of the methyl groups and the total AcH selectivity were calculated as follows:

$$\text{Conversion of the } CH_3 \text{ groups (mole \%)} = \frac{\text{Moles of (MeOH + AcOMe} \times 2) \text{ charged} - \text{moles of the product (MeOH + AcOMe} \times 2 + \text{dimethoxyethane} \times 2)}{\text{Moles of (MeOH + AcOMe} \times 2) \text{ charged}} \times 100$$

$$\text{Total AcH selectivity (mole \%)} = \frac{\text{Moles of the product (AcH + dimethoxyethane)}}{\text{Moles of (MeOH + AcOMe} \times 2) \text{ charged} - \text{moles of the product (MeOH + AcOMe} \times 2 + \text{dimethoxyethane} \times 2)} \times 100$$

The above method of calculation was used because dimethoxyethane easily hydrolyzes to 1 molecule of AcH and 2 molecules of MeOH.

TABLE 1

| Example | 1 | 2 | 3 |
|---|---|---|---|
| Amounts charged | | | |
| MeOH (mole) | 0.3121 | 0.3121 | 0.3121 |
| AcOMe (mole) | 0.1485 | 0.1485 | 0.1485 |
| Catalyst (mole) species | CoI₂ 0.0040 | CoI₂ 0.0080 | CoI₂ 0.0080 |
| AcOMe/MeOH weight ratio | 1.1 | 1.1 | 1.1 |
| Total CH₃ groups (moles) | 0.6091 | 0.6091 | 0.6091 |
| Co or I/CH₃ groups (mg · atom/mole) | Co I 6.6 13.2 | Co I 13.1 26.2 | Co I 13.1 26.2 |
| Reaction temperature (°C.) | 123 | 145 | 145 |
| Reaction time (hr) | 2.0 | 0.67 | 1.0 |
| Intended components in the product | | | |
| MeOH (mole) | 0.1402 | 0.1449 | 0.1054 |
| AcH (mole) | 0.0614 | 0.0980 | 0.1310 |
| EtOH (mole) | trace | trace | trace |
| AcOMe (mole) | 0.1481 | 0.1460 | 0.1382 |
| AcOH (mole) | 0.0050 | 0.0015 | 0.0020 |
| Dimethoxyethane (mole) | 0.0354 | 0.0242 | 0.0310 |
| Conversion of CH₃ groups (mole %) | 16.7 | 20.3 | 27.1 |
| Total AcH selectivity (mole %) | 95.2 | 98.8 | 98.1 |
| CH₃ group balance (mole %) | 100 | 98.3 | 99.8 |

| Example | 4 | 5 | |
|---|---|---|---|
| Amounts charged | | | |
| MeOH (mole) | 0.3121 | 0.3121 | |
| AcOMe (mole) | 0.2700 | 0.1485 | |
| Catalyst (mole) species | CoI₂ 0.0048 | Co₂(CO)₈ 0.00020 | I₂ 0.0040 |
| AcOMe/MeOH weight ratio | 2.0 | 1.1 | |
| Total CH₃ groups (moles) | 0.8521 | 0.6091 | |
| CO or I/CH₃ groups (mg · atom/mole) | Co I 5.6 11.2 | Co I 6.6 13.1 | |
| Reaction temperature (°C.) | 155 | 155 | |
| Reaction time (hr) | 0.67 | 0.67 | |
| Intended components in the product | | | |
| MeOH (mole) | 0.1300 | 0.1210 | |
| AcH (mole) | 0.1115 | 0.0807 | |
| EtOH (mole) | trace | 0.0010 | |
| AcOMe (mole) | 0.2420 | 0.1390 | |
| AcOH (mole) | 0.0026 | 0.0032 | |
| Dimethoxyethane (mole) | 0.0404 | 0.0410 | |
| Conversion of CH₃ groups (mole %) | 18.5 | 21.0 | |
| Total AcH selectivity (mole %) | 96.3 | 95.1 | |
| CH₃ group balance (mole %) | 99.7 | 99.6 | |

TABLE 2

| Comparative Example | 1 | 2 | 3 |
|---|---|---|---|
| Amounts charged | | | |
| MeOH (mole) | 0.4682 | 0.3121 | 0.3121 |
| AcOMe (mole) | none | 0.0405 | 0.1485 |
| Catalyst species (mole) | CoI₃ 0.0048 | CoI₂ 0.0040 | CoI₂ 0.0080 |
| AcOMe/MeOH weight ratio | — | 0.30 | 1.1 |
| Total CH₃ groups (mole) | 0.4682 | 0.3931 | 0.6091 |
| Co or I/CH₃ groups (mg · atom/mole) | Co I 10.3 20.6 | Co I 10.2 20.4 | Co I 13.1 26.2 |
| Reaction temperature (°C.) | 145 | 145 | 165 |
| Reaction time (hr) | 0.67 | 1.0 | 0.67 |
| Intended components in the product | | | |
| MeOH (mole) | 0.2541 | 0.1295 | 0.1184 |
| AcH (mole) | 0.0451 | 0.0640 | 0.0742 |
| EtOH (mole) | 0.0011 | 0.0082 | 0.0100 |
| AcOMe (mole) | 0.0240 | 0.0361 | 0.1268 |
| AcOH (mole) | 0.0023 | 0.0068 | 0.0066 |
| Dimethoxyethane (mole) | 0.0350 | 0.0334 | 0.0413 |
| Conversion of CH₃ groups (mole %) | 30.8 | 31.7 | 25.4 |
| Total AcH selectivity (mole %) | 55.5 | 78.2 | 74.7 |
| CH₃ group balance (mole %) | 99.4 | 96.9 | 96.3 |

| Comparative Example | 4 | 5 |
|---|---|---|
| Amounts charged | | |
| MeOH (mole) | 0.3121 | 0.3121 |
| AcOMe (mole) | 0.1485 | 0.1485 |
| Catalyst (mole) species | Co₂(CO)₈ I₂ 0.004 0.0019 | Co₂(CO)₈ I₂ 0.0020 0.0100 |
| AcOMe/MeOH weight ratio | 1.1 | 1.1 |
| Total CH₃ groups (mole) | 0.6091 | 0.6091 |
| Co or I/CH₃ groups (mg · atom/mole) | Co I 13.1 6.2 | Co I 6.6 32.8 |
| Reaction temperature (°C.) | 155 | 155 |
| Reaction time (hr) | 0.67 | 0.67 |
| Intended components in the product | | |
| MeOH (mole) | 0.1341 | 0.1135 |
| AcH (mole) | 0.0386 | 0.0650 |
| EtOH (mole) | 0.0084 | 0.0020 |
| AcOMe (mole) | 0.1476 | 0.1343 |
| AcOH (mole) | 0.0055 | 0.0130 |
| Dimethoxyethane (mole) | 0.0372 | 0.0447 |
| Conversion of CH₃ groups (mole %) | 17.3 | 22.6 |
| Total AcH selectivity (mole %) | 71.9 | 79.7 |
| CH₃ group balance | 97.4 | 97.9 |

What we claim is:

1. In a process for producing acetaldehyde which comprises reacting a mixture of methanol and methyl acetate with carbon monoxide and hydrogen in the presence of a cobalt-iodine catalyst, the improvement wherein methyl acetate is used in an amount of 0.5 to 4 parts by weight per part by weight of methanol, cobalt and iodine are used in an amount of 2 to 100 milligram-atoms and 8 to 200 milligram-atoms, respectively, per mole of the entire methyl groups in the methanol and methyl acetate, 1 to 4 iodine atoms being present per cobalt atom, and the reaction is carried out at a temperature of from 80° to 160° C. and a pressure of from 50 to 300 kg/cm$^2$.

2. The process of claim 1 wherein $\frac{1}{4}$ to 4 moles of hydrogen is used per mole of carbon monoxide.

3. The process of claim 2 wherein hydrogen and carbon monoxide are supplied by synthesis gas.

4. The process of claim 1 wherein the catalyst consists essentially of cobalt iodide.

5. The process of claim 1 wherein the reaction temperature is 115° to 155° C.